United States Patent [19]

Evans, Sr.

[11] 4,441,491

[45] Apr. 10, 1984

[54] PRESSURE RELIEF VALVE SYSTEM FOR PENILE IMPLANT DEVICE

[76] Inventor: Alvin S. Evans, Sr., 234 Shubert Ave., Runnemede, N.J. 08078

[21] Appl. No.: 407,969

[22] Filed: Aug. 13, 1982

[51] Int. Cl.³ .............................................. A61F 5/00
[52] U.S. Cl. ............................................. 128/79; 3/1
[58] Field of Search ....................... 128/79, 79 A; 3/1; 604/99

[56] References Cited

U.S. PATENT DOCUMENTS

| | | | |
|---|---|---|---|
| 3,954,102 | 5/1976 | Buuck | 128/79 A |
| 4,201,202 | 5/1980 | Finney et al. | 3/1 X |
| 4,224,934 | 9/1980 | Scott et al. | 128/79 A |

*Primary Examiner*—Stephen C. Pellegrino
*Attorney, Agent, or Firm*—Caesar, Rivise, Bernstein & Cohen, Ltd.

[57] ABSTRACT

A pressure relief valve system for a prosthetic penile implant device where the penile implant device basically includes bladder means, a reservoir, and a pump and valve assembly. The bladder means is implanted in the penis while the reservoir, and the pump and valve assembly are implanted at a remote location thereto. The pump and valve assembly provide means for pumping water from the reservoir into the bladders to obtain a simulated erection and for pumping water from the bladders to the reservoir to obtain a flaccid penis. The pressure relief valve system of the instant invention is used in combination with the pump and valve assembly to prevent excessive pressure from developing within the bladder means so as to cause injury. The pressure relief valve system comprises a primary valve and a secondary valve. The primary valve enables water to pass from the pump means to the reservoir, bypassing the bladder means whenever the water pressure adjacent the pump means exceeds a predetermined threshold amount, while the secondary valve enables water to pass from the bladder means to the reservoir whenever the water pressure adjacent the bladder means exceeds a second, generally higher amount.

10 Claims, 6 Drawing Figures

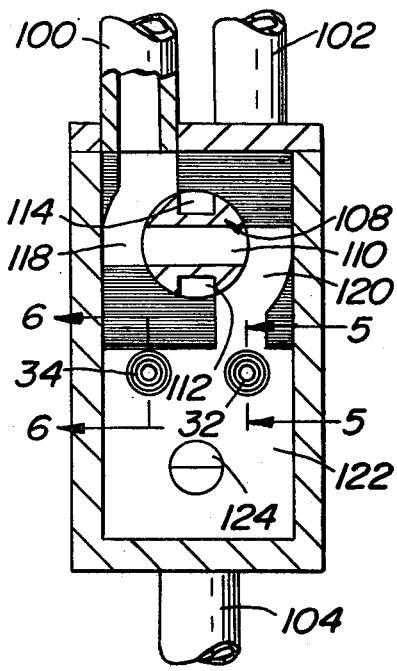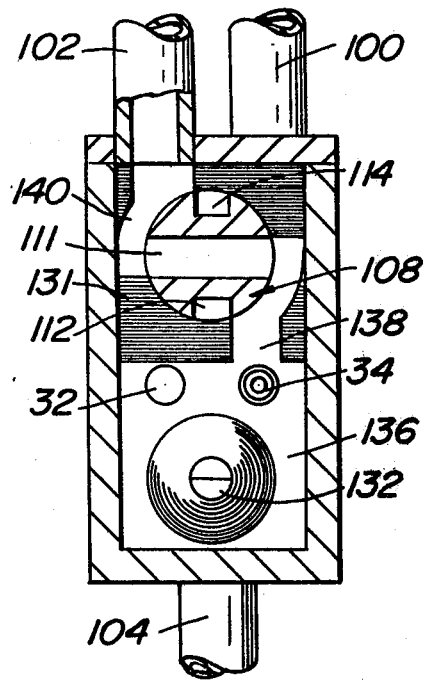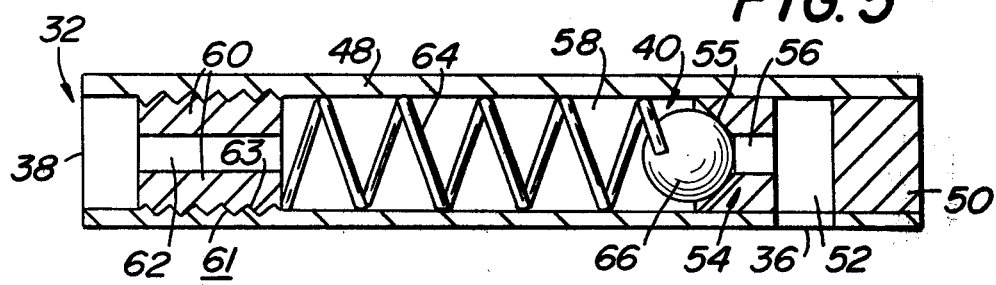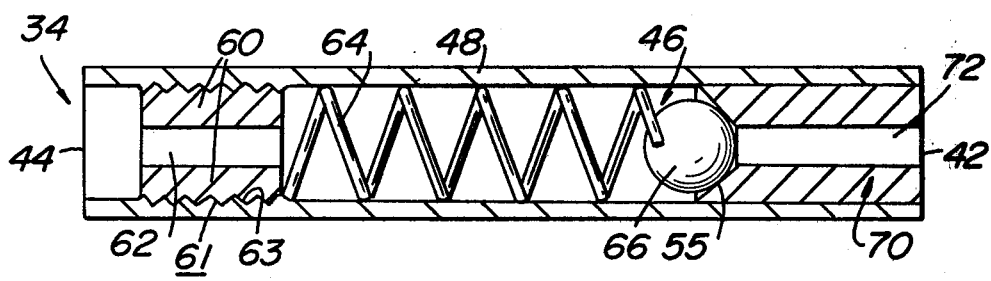

PRESSURE RELIEF VALVE SYSTEM FOR PENILE IMPLANT DEVICE

BACKGROUND OF THE INVENTION

This invention relates generally to prosthetic devices and more particularly to a pressure relief valve system for use in combination with a penile implant device.

In order to remedy the effects of certain types of functional impotency, implants have been developed for surgical insertion in a penis to simulate a natural erection.

In that regard, various surgical implants and implant techniques entail implanting inflatable bladders in each corpus cavernosum of the penis. Contained in the prior art are various patents relating to penile implant devices. Several examples of such devices are disclosed in U.S. Pat. Nos. 3,853,122 (Strauch, et al.); 3,954,102 (Buuck) and 4,009,711 (Uson).

A preferred type of penile implant device and a pump and valve assembly which comprises a portion of the device are disclosed and claimed in my co-pending U.S. patent applications Ser. No. 313,114, filed on Oct. 20, 1981, now U.S. Pat. No. 4,424,807 and Ser. No. 366,447 filed on Apr. 7, 1982, now U.S. Pat. No. 4,404,968 respectively, both of whose disclosures are incorporated by reference herein.

The implant device disclosed in said patent application basically comprises bladder means, the pump and valve assembly and a reservoir. More specifically, the implant device disclosed in said patent application includes a pair of hollow, enclosed bladders each having an access port to the interior thereof and formed of a membrane of a thin, very flexible material. Each of said bladders is capable of inflation by the introduction of a fluid (e.g., water) therein through its port. A respective one of the bladders is located in the passageway of each corpus cavernosum. When the bladders are filled with the fluid they are inflated from their flaccid state to a predetermined volume without causing the bladder membrane to undergo tension. This predetermined volume is sufficiently great to cause the corpora cavernosa to expand so that the fiberous tissue envelope surrounding the copora cavernosa encompasses another predetermined volume, whereupon the fiberous tissue becomes tense and the penis becomes hard and erect.

The pump and valve assembly comprises a rotor and uni-directional valve means such that the fluid is able to flow from a reservoir to the bladders when the rotor is in a first position and from the bladders to the reservoir when the rotor is in a second position. To that end, the valve means precludes the fluid from flowing in a reverse direction once the fluid has passed either to the reservoir or to the bladders, respectively. Moreover, pump means are utilized in order to pump additional fluid either into the bladders to obtain a fully erect penis or alternativly, to pump fluid out of the bladders and into the reservoir to obtain a flaccid penis. The pump and valve assembly is generally implanted within the scrotum, although alternative embodiments of the assembly entail the valve assembly portion of the pump and valve assembly being implanted in the abdominal cavity, adjacent the reservoir.

Although the pump and valve assembly disclosed and claimed in the above mentioned application is satisfactory for its intended purpose, there is the inherent danger that the user of the device might inadvertantly pump too much fluid into the bladders so as to either damage the penile implant device or cause injury to the tissue of the penis.

Similar problems, namely, injury to either the implant device or to the tissue of the penis can also result when excessive pressure develops within the device as a result of the bladders being squeezed either inadvertantly or as a result of vigorous sexual activity.

OBJECTS OF THE INVENTION

Accordingly, it is a general object of the instant invention to provide a penile implant pressure relief valve system which overcomes the disadvantages inherent in the prior art penile implant devices.

It is another object of the invention to provide a pressure relief valve system for bladder-based penile implant devices which protects both the bladder(s) of the device as well as the tissue of the penis from injury attributable to over-inflation.

It is a further object of the invention to provide a relief valve system for bladder-based penile implant devices which further protects the bladder(s) of the device as well as the tissue of the penis from injury when the implanted bladders of the device are squeezed.

It is still a further object of the invention to provide a pressure relief valve system for a bladder-based penile implant device which is compact, simple in construction, and readily utilized in combination with existing penile implant devices.

SUMMARY OF THE INVENTION

These and other objects of the instant invention are achieved by providing a pressure relief valve system which is used in combination with a prosthetic penile implant device to simulate a natural erection. To that end, the penile implant device includes bladder means which are implanted within the penis, a fluid containing reservoir, valve means and pump means which are respectively implanted at remote locations thereto. The valve means is arranged to provide uni-directional fluid communication from the bladder means to the reservoir, thus enabling fluid to pass from the bladder means to the reservoir whenever the fluid pressure inside the bladder means is greater than a predetermined amount. Furthermore, the valve means precludes fluid from passing therethrough whenever the pressure inside the bladder means is not greater than that amount, to establish a maximum amount of fluid pressure which may be present within the bladder means. Thus, the bladder means and the tissue of the penis are protected from injury attributable to excessive pressure within the bladder means.

DESCRIPTION OF THE DRAWING

Other objects and many of the attendant advantages of this invention will be readily appreciated as the same becomes better understood by reference to the following detailed description when considered in connection with the accompanying drawing wherein:

FIG. 3 is a sectional view taken along line 3—3 of FIG. 2;

FIG. 4 is a sectional view taken along line 4—4 of FIG. 2;

FIG. 5 is an enlarged sectional view taken along line 5—5 of FIG. 3; and

FIG. 6 is an enlarged sectional view taken along line 6—6 of FIG. 3.

DETAILED DESCRIPTION OF THE PREFERRED EMBODIMENT

Figure 1:
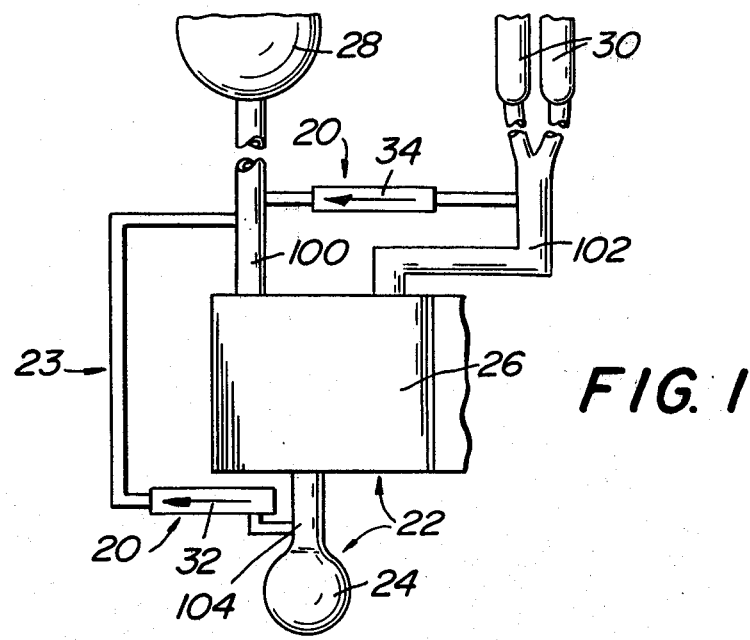
FIG. 1 is a schematic diagram of a penile implant device, which includes the pressure relief valve system of the instant invention.

Referring now to the various figures of the drawing wherein like reference characters refer to like parts, there is generally shown at 20 in FIG. 1 a pressure relief valve system connected to the pump and valve assembly of a penile implant device 23 like that constructed and arranged in accordance with the teachings of my two previously mentioned patent applications.

Still referring to FIG. 1, the penile implant device 23 basically includes a pump and valve assembly 22, a reservoir 28 and bladder means 30. The pump and valve assembly 22 includes a pump mechanism 24 and a valve assembly 26. The bladder means 30 comprises a pair of hollow enclosed bladders each having an access port to the interior thereof and formed of a thin, very flexible membrane. Each bladder 30 is implanted within a respective corpus cavernosum of the penis.

The reservoir comprises a hollow body formed of a flexible membrane which is implanted within the abdominal cavity. The reservoir is arranged to hold a liquid, e.g., water, therein.

The pump mechanism 24 is implanted in the scrotum while the valve assembly 26 is generally implanted either in the abdominal cavity or in the scrotum. The reservoir is connected to the pump and valve assembly 22 via tubing to provide the means for pumping fluid (e.g., water) from the reservoir 28 to the bladder means 30 (to inflate the bladder means) or from the bladder means to the reservoir (to deflate the bladder means). In particular to obtain a simulated erection water is pumped from the reservoir 28 into the bladder means 30 and to obtain a flaccid penis water is pumped from the bladder means 30 back into the reservoir.

The pressure relief valve system 20 of the instant invention is used in combination with the pump and valve assembly 22 to prevent excessive amounts of water pressure from developing within the bladders 30 or elsewhere within the penile implant device 23 so as to cause injury either to the tissue of the penis or to the implanted device, especially the bladders.

The pressure relief valve system 20 of the instant invention comprises a pair of uni-directional pressure relief valves, namely, a primary valve 32 and a secondary valve 34. The primary valve 32 basically comprises an inlet port 36, an outlet port 38 and regulator means 40. The secondary valve 34 also basically comprises an inlet port 42, an outlet port 44 and regulator means 46.

With regard to the primary valve 32, the regulator means 40 controls the flow of water from the inlet port 36 to the outlet port 38. Referring to FIG. 1, it can be seen that the inlet port 36 is in fluid communication with the pump 24 and the outlet port 38 is in fluid communication with the reservoir 28. By virtue of these connections, the valve 32 provides means for fluid communication between these respective members of the penile implant device 23. The regulator means 40 enables fluid communication to occur only when the fluid pressure at the inlet port 36 of the valve means exceeds a predetermined threshold amount e.g., approximately 2 pounds per square inch (0.14 kg./sq. cm.). Thus, the valve 32 operates as a pressure relief valve in that it permits water to pass from a higher pressure area to a lower pressure area when the pressure in the higher pressure area exceeds a predetermined level.

With regard to the secondary valve 34, the regulator means 46 controls the flow of water from its inlet port 42 to its outlet port 44. The inlet port 42 is in fluid communication with the bladder means 30 and the outlet port 44 is in fluid communication with the reservoir 28. Thus, the valve 34 provides means of fluid communication from the bladder means 30 to the reservoir 28. The regulator means 46 permits water to flow from the bladder means to the reservoir whenever the pressure at the inlet port 42 exceeds a predetermined threshold amount e.g., approximately 3 pounds per square inch (0.21 kg./sq. cm.). The valve 34 also functions as a pressure relief valve in that it enables water to pass from a higher pressure area to a lower pressure area whenever the pressure in the higher pressure area exceeds a certain level.

Figure 2:
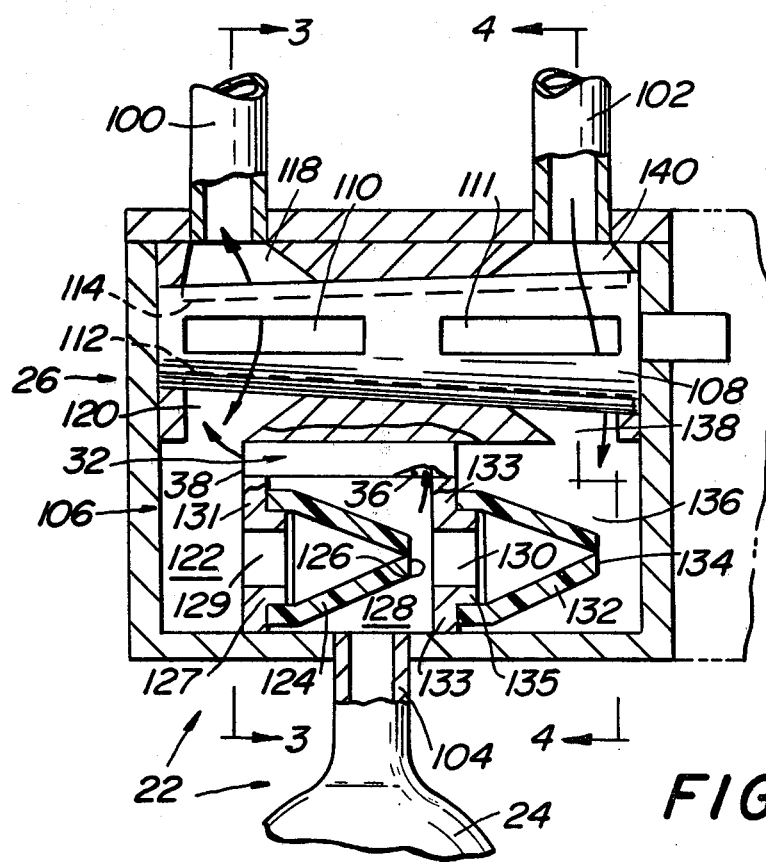
FIG. 2 is an enlarged side elevational view, partially in section, of a pump and valve assembly including the pressure relief valve system of the instant invention.

Referring to FIG. 2, in order to fully appreciate the construction and operation of the pressure relief valve system 20 of the instant invention it is necessary to consider the system in the context of the environment in which it preferably operates, namely, inside the housing 106 of the penile implant pump and valve assembly 22 like that shown and claimed in my co-pending application Ser. No. 366,447 filed on Apr. 7, 1982. As set forth in that application and as will be summarized hereinafter, in order to obtain a simulated erection using the pump and valve assembly 22, a rotor 108 of the assembly is rotated by rotational means to the position shown in FIG. 2. The rotor 108 is a generally cylindrical, frusto conical member situated within a bore in the housing 106 of the pump and valve assembly and includes a pair of generally rectangular slots 110 and 111, respectively, extending diametrically through the rotor. The slots are coplaner with each other but located at different longitudinal positions along the curved surface of the rotor 108. The rotor 108 also includes a pair of elongated recesses 112 and 114, respectively, which are used for transporting water from the bladder means 30 back to the reservoir 28 to terminate an erection, when desired.

Since the reservoir is under a more or less constant abdominal pressure, when the rotor 108 is rotated to the position shown in FIGS. 2, 3 and 4 the water contained therein flows through the tube 100 and into a chamber 118 of the housing 106 of the pump and valve assembly. The water then passes from the chamber 118, through the slot 110 in the rotor, through an upper port area 120 and into another chamber 122. Contiguous with the chamber 122 is a check valve 124 which enables water to flow in only one direction therethrough. Thus, communication between the chamber 122 and another chamber 128 is established, with the direction of communication being from left to right as shown in FIG. 2. The valve 124 is secured on a flange 127 extending about a port 129 in a wall 131. The wall 131 separates the chamber 122 from a second chamber 128 and to which an outlet slit 126 of the valve 124 is in communication. The tube 104, which is in fluid communication with the pump mechanism 24 is also in fluid communication with the chamber 128.

As will readily be appreciated by those skilled in the art, with the arrangement just described fluid is able to pass from chamber 122 into chamber 128 while fluid within chamber 128 is precluded from passing in a reverse direction from chamber 128 into chamber 122. Chamber 128 is also in fluid communication with the pump mechanism 24 by means of a tube 104. In addition, chamber 128 is contiguous to an opening 130 in a wall 133 similar to wall 131.

The valve 132 is identical to valve 124 and is mounted on a flange 135 on the wall 133 and extends about an opening 130. The outlet slit 134 of the valve is in communication with another chamber 136. Thus, valve 132 permits fluid to pass from intermediate chamber 128 into chamber 136 while at the same time precluding fluid from passing in the reverse direction.

Thus, when the rotor 108 is in the position shown in FIGS. 2, 3 and 4 water within chamber 136 is enabled to flow through an outlet port 138 at the top of chamber 136, through slot 111 in the rotor and into a passageway 140 at the top of the housing contiguous with the tube 102. The water then flows into tube 102 to fill the bladders 30 which are implanted in the penis.

When the rotor is first positioned as shown in FIGS. 2, 3 and 4, the water naturally begins to flow from the reservoir 28 through the valves 124 and 132, respectively, in the path just described and to the bladders 30 under the ambient body pressure exerted on the reservoir. Once pressure equilibrum is reached, that is the pressure produced by the body on the reservoir is equal to the pressure on the bladders within the penis, no further water flow into the bladders occurs and the penis thus assumes a semi-erect state.

The pump mechanism 24 is utilized to obtain a fully erect penis by further filling the bladders through the valve system. To that end, the pump mechanism 24 basically comprises a hollow bulb-like member formed of a resilient material and arranged to be squeezed manually. Since the bulb 24 is in fluid communication with the chamber 128, via tube 104, the squeezing of the bulb causes water within chamber 128 to flow through the valve 134 into chamber 136 and through the connecting fluid path into the bladders. In addition, the pumping action reduces the pressure within the chamber 128 as compared to chamber 122 thereby drawing additional water from the reservoir, through a tube 100, into the chamber 122 and then into the chamber 128. Thus by repeated squeezing and releasing of the bulb 24, sufficient water can be pumped from the reservoir into the bladders to effect the attainment of a viable erection. As mentioned and as shall be described in detail later, the pressure relief valve system 20 of the instant invention provides means for preventing fluid pressure in excess of a predetermined amount from being pumped into the bladders 30.

As should readily be appreciated from the foregoing discussion, fluid pumped from the reservoir into the bladders is generally precluded from flowing back into the reservoir by the action of the uni-directional valves 124 and 132. The secondary pressure relief valve 34 of the instant invention includes means, which shall be described in detail later, to allow fluid to flow from the bladders back into the reservoir 28 in the event that the bladders are squeezed or if other conditions arise irrespective of the action of pump 24, tending to increase the fluid pressure within the bladders to an excessive level, e.g., greater than 3 pounds per square inch (0.21 kg./sq. cm.).

In order to terminate the erection (i.e., move the water out of the bladders and back into the reservoir), the rotor 108 is rotated to in the opposite rotational direction to enable the water to first naturally flow and then be pumped, respectively, from the bladder means 30 to the reservoir 28 as set forth in my above mentioned co-pending pump and valve assembly patent application.

Referring now to FIG. 1, it should readily be appreciated that the primary pressure relief valve 32 and the secondary pressure relief valve 34 provide means for bypassing or shunting the check valves 124 and 132 to enable water to return to the reservoir in the event that excessive pressure builds-up within the bladder means or adjacent the pump mechanism 24 in the pump and valve assembly 22. It should further be appreciated that under normal conditions (i.e., where the bladders 30 are not being squeezed), when an erection is being maintained, the pressure adjacent the pump mechanism is generally equal to that of the bladders.

Referring to FIG. 2, the primary pressure relief valve 32 is located in the housing 106 of the pump and valve assembly 22 with its inlet port 36 in fluid communication with the chamber 128 and its outlet port 38 in fluid communication with the chamber 122. Specifically, the valve 32 is mounted in a bore passing through the walls 131 and 133, respectively, of the housing. The valve 32 is disposed generally parallel and adjacent the rotor 108 to form a partial ceiling to chamber 128.

The secondary pressure relief valve 34 (not shown in FIG. 2 and only partially shown in FIGS. 3 and 4) is disposed parallel to and generally behind the primary valve 32. Furthermore, the valve 34 is in fluid communication with chambers 136 and 122, respectively. The inlet port 42 of the secondary relief valve is in fluid communication with chamber 136 while the outlet port 48 is in fluid communication with the chamber 122. The secondary relief valve 34 is located within a bore in the walls 131 and 133, respectively, of the housing.

Referring to FIG. 5, the primary valve 32 comprises a generally hollow cylindrical sleeve 48, with one end surface being generally open to form the outlet port 38 and the opposite end surface being sealed by an end cap 50. The interior of the sleeve is denoted by the reference numeral 58. A circular inlet port 36 extends through the cylindrical side surface of the sleeve adjacent the end cap 50. This port is in fluid communication with an inlet cavity 52 in the sleeve 48. Adjacent and in fluid communication with the inlet cavity 52 is a valve seat member 54. The member 54 comprises a cylindrical plug having a hollow passageway 56 passing through its center. The passageway 56 is flared at its inner end to form a conical valve seat surface 55 whose function shall be described later. When the valve 32 is in its "open" state, as shall be described later, the passageway 56 is in fluid communication with both the inlet cavity 52 and the generally hollow interior section 58 of the sleeve.

The opposite end surface of the sleeve 48 is open so as to define the outlet port 38. The interior surface of the sleeve adjacent port 38 is internally threaded at 61. A retainer plug 60 having a mating externally threaded surface is threadily disposed within the sleeve. The plug 60 is a generally cylindrical member having a hollow passageway 62 through the center thereof. The passageway 62 is in fluid communication with both the outlet port 38 and the hollow interior section 58 of the sleeve.

As can be seen in FIG. 5, fluid communication between the valve's inlet port 36 and outlet port 38 is controlled by the regulator means 40. The regulator means 40 basically comprises a compression spring 64 and a ball 66. One end of the spring 64 presses against the ball 66 and the opposite end of the spring 64 presses against the retainer plug 60.

It should be mentioned that an alternative embodiment of the system 20 would include a spring which is attached to a ball at one end and/or to the retainer plug at its opposite end.

As should readily be appreciated, the spring produces a bias force which tends to push the ball 66 against the conical valve seat surface 55. When the ball 66 abuts the valve seat fluid is precluded from passing from the passageway 56 to the interior section 58 of the valve 32. The valve is thus "closed."

When the pressure of the water at the inlet port causes a force to be exerted on the ball 66 in excess of the bias force of the spring 64, the spring commences compressing, i.e., moving further within the hollow interior 58 of the sleeve. Thus, the ball 66 is off of the valve seat 55 and fluid is able to flow through the valve by passing from the inlet port 36, through the hollow interior section 58, through the passageway 62 in the retainer plug 60, to and then out the outlet port 38. Under these circumstances the valve 32 is open.

As a result of the conical construction of the valve seat 55, the size of the opening or passageway between the valve seat and the ball 66 is determined by the amount by which the fluid pressure adjacent the inlet port 36 exceeds the biasing force which is exerted on the ball 66 by the spring 64. In other words, the greater the disparity between the biasing force and the fluid pressure, respectively, the further the ball 66 is pushed away from the passageway 56.

Furthermore, the farther the ball is pushed away from the passageway 56 (within certain limits which are not critical with regard to the operation of the instant invention), the greater is the amount of fluid which is able to pass through the valve 32 per unit of time, e.g., the greater the flow rate. It should be pointed out however, that the graduated flow characteristic as just described is not at all essential in order for the valve system 20 to function or perform as desired by merely reflects the physical construction of one embodiment of regulator means 40 which can be used.

In that regard, alternative embodiments of the foregoing invention which also perform quite satisfactorily do not maintain a graduated flow characteristic but include valves constructed to be either in a completely open or a completely closed state of operation, depending upon whether some preselected amount of pressure has been exceeded.

As should readily be appreciated from the foregoing discussion, the ball 66 does not touch the valve seat 54 until such time that the pressure adjacent the inlet port 36 has sufficiently dropped so as to be less than the value which maintains the valve 32 in its open state. As should further be appreciated from FIG. 5, the valve 32 is uni-directional, i.e., it precludes the flow of fluid from the outlet port 38 to the inlet port 36. This necessarily results since the passage of water in a reverse direction (i.e., from the outlet port 38 to the inlet port 36) would cause the ball 66 to be pushed into the conical end portion 55 of the valve seat 54, thus closing what would be the path of fluid communication.

The amount of pressure necessary to open the valve 32 is readily adjusted by means of either increasing or decreasing the effective length of the spring 64. This is accomplished by moving the retainer plug 60 either away from or closer to, respectively, the valve seat 54. The retainer plug 60 is readily moved as such by rotating or threading the retainer plug 60 either in a counter-clockwise or a clockwise direction, respectively. Rotation as such is readily achieved by using a hex wrench or other small tool.

Referring to FIG. 6, the secondary pressure relief valve 34 is in all respects quite similar to the primary valve 32 except that instead of having an end cap and an inlet cavity, the secondary valve 34 comprises a valve seat 70 having an elongated passageway 72 through the center thereof which is in direct fluid communication with its inlet port 42. The inlet port 42 is situated on one of the end surfaces of the sleeve rather than being situated on the cylindrical side surface as is the case with the primary valve 32. The operation and construction of the secondary valve 34 is otherwise identical to that of the primary valve 32.

Having described the structure and the manner in which the primary and secondary valves 32 and 34, respectively, are arranged within the pump and valve assembly 22, the operation of the pressure relief valve system 20 shall now be described in detail.

The primary valve 32 precludes the water pressure in the vicinity of the pump mechanism 24 from exceeding a first predetermined or threshold level, thus insuring against overinflation of the bladders. When this predetermined amount of pressure is exceeded the regulator means 40 of the primary valve 32 causes the valve to open, thus enabling the water to pass through the valve 32 and back into the reservoir 28, rather than passing through the check valve 134 to the bladders 30, as would otherwise occur.

The secondary valve serves a somewhat different purpose in that it generally insures against excessive pressure within the bladders 30 attributable not to the pumping action of the pump mechanism 24 but rather to compression or squeezing of the penis and hence of the bladders which might result from various conditions. Thus, the secondary relief valve 34 is arranged to enable water to pass from the bladders 30 to the reservoir 28, bypassing the check valve portion 132 of the pump and valve assembly, whenever the pressure within the bladders exceeds a second predetermined amount. This second predetermined amount of pressure is generally substantially higher than the threshold pressure, i.e., the amount necessary to open the primary valve 32.

The reason for this disparity should readily be appreciated in view of the purpose or function served by the respective valves. In that regard, the primary valve 32 establishes the maximum pressure to which the bladders may be inflated while the secondary valve 34 establishes the maximum pressure which the bladders 30 can maintain at a time subsequent to their having been inflated. Typically, the elevating factor causing the pressure in the bladders 30 to increase beyond that which is established by the pumping action of the pump mechanism 24, is attributable to the squeezing of the bladders which might occur during vigorous sexual activity.

Since water passing through the secondary pressure relief valve 34 to the reservoir is precluded from passing back to the bladders 30 absent additional pumping action of the pump mechanism, it is desirable to have the secondary relief valve remain in a closed state of operation absent an exceptionally large increase in pressure. Otherwise, the penis would not remain fully erect during sexual intercourse. Moreover, if only a single pressure relief valve were to be used, namely only the secondary valve 34, inflation of the bladders 30 to its maximum level as established by the valve 34 would almost invariably result in a gradual decrease in the amount of water in the bladders during sexual activity. Conversely, if only the primary valve 32 were used, the system would not provide means for relieving pressure should extraordinarily high pressure build-up within the bladders.

For the foregoing reasons, although either the primary valve 32 or the secondary valve 34 may readily be utilized alone without the other in the pump and valve assembly 22, the preferred embodiment of the invention 20, entails the utilization of both of these valves 32 and 34.

Referring to FIGS. 3 and 4, the actual details of the flow of water through the penile implant system shall be described now.

With regard to the primary pressure relief valve 32, when the pressure in chamber 128 (FIG. 2) exceeds the predetermined threshold amount, the regulator means 40 causes the valve 32 to open. Since the pressure inside chamber 128 is significantly greater than the pressure within chamber 122 (or the pressure in the bladders 30), water passes through the primary valve 32 and into chamber 122. As can best be appreciated from FIG. 3, the water then passes into chamber 120, through the slot 110 and into the upper chamber 118. Water then passes from the upper chamber 118, through the tube 100 and back into the reservoir 28 until such time that the pressure within the chamber 128 has dropped below the predetermined threshold amount, causing the valve 32 to close.

Additional pumping of the pump mechanism 24 causes the primary valve 32 to open. This action prevents additional water from being pumped into the bladders 30. Thus, water is pumped into the bladders until the resulting pressure inside the chamber 128 and in the bladders 30 has reached the predetermined amount established by the primary valve 32.

Since the bladders 30 are in fluid communication with chamber 138 through the interconnecting tube 102, chamber 140 and slot 111, when the pressure within the bladders 30 exceeds the predetermined threshold amount, the regulator means 46 causes the valve 34 to open. When this happens, water passes from the bladder means 30, through tube 102, into chamber 140, through the slot 111 and into the chamber 138. The water then passes into the inlet port 42, through the valve 34 and out of the outlet port 44. Since the outlet port 44 of the secondary valve 34 is in fluid communication with chamber 122, the fluid then passes from chamber 122 to the reservoir 28 in a similar manner to the manner described for the primary valve 32. Furthermore, water continues to pass in this direction until such time that the pressure within the bladders 30 is reduced to a level less than the second predetermined threshold amount. At this time the secondary valve 34 assumes a closed state and no additional water passes through the valve 34 to the reservoir unless and until the pressure within the bladder means again exceeds the threshold level.

As will be appreciated from the foregoing, the pressure relief valve system 20 of the instant invention is relatively simple in construction and is quite effective as means for preventing excessive fluid pressure from occurring within a penile implant device.

Without further elaboration the foregoing will so fully illustrate my invention that others may by applying current or future knowledge readily adpat the same for use under various conditions of service.

I claim:

1. A pressure relief valve system for use in combination with a penile implant device which is used for simulating a natural erection, wherein said penile implant device includes bladder means which are implanted within the penis, a fluid containing reservoir and primary unidirectional valve means which are respectively, implanted at remote locations thereto and pump means which is implanted in the scrotum, said primary unidirectional valve means permitting fluid to pass from said pump means to said bladder means while precluding fluid from passing in the opposite direction, wherein said system comprises pressure relief valve means arranged to provide uni-directional fluid communication between said pump means and said reservoir, said pressure relief valve means being interposed in the path of fluid communication between said pump means and said primary unidirectional valve means, thus enabling fluid to bypass said primary unidirectional valve means and said bladder means by passing from said pump means to said reservoir whenever said fluid pressure adjacent said pump means is greater than a first predetermined amount and precluding fluid from passing therealong whenever said pressure is less than said first predetermined amount, said pressure relief valve means thus establishing a maximum amount of fluid pressure which can be pumped into said bladder means with said pump means, yet not limiting the amount of pressure which can otherwise be maintained in said bladder means.

2. The system of claim 1, further comprising a second pressure relief valve arranged to provide uni-directional fluid communication between said bladder means and said reservoir, enabling fluid to pass therethrough in passing from said bladder means to said reservoir whenever the fluid pressure inside said bladder means is greater than a second predetermined amount and precluding fluid from passing therethrough whenever said pressure is not greater than said amount.

3. The system of claim 2, wherein said second predetermined amount is greater than said first predetermined amount such that when said pump means is utilized to inflate said bladder means to said first predetermined amount of pressure, fluid passes through said second valve means only when said bladder means incurrs additional pressure with said additional pressure being generally attributable to compression of said bladder means.

4. The system of claim 3, wherein said first and second valve means each comprises an inlet port, an outlet port and regulator means with said regulator means both controlling the passage of fluid from said inlet port to said outlet port and precluding the passage of fluid in the reverse direction.

5. The system of claim 4, wherein said regulator means comprises a spring and a ball which communicates with said spring, such that when said spring is in an extended position, said ball is in a first location to preclude fluid from passing through said valve means and when said spring is compressed, said ball moves away from said first location to enable fluid to pass through said valve means.

6. The system of claim 5, further comprising rotatable means for adjusting the tension of said spring.

7. A pressure relief valve system for use in combination with a penile implant device which is used for simulating a natural erection, wherein said penile implant device includes bladder means which are implanted within the penis, a fluid containing reservoir and valve means which are respectively, implanted at remote locations thereto and pump means which is implanted in the scrotum, wherein said system comprises first and second pressure relief valve means, said first pressure relief valve means is arranged to provide unidirectional fluid communication between said pump means and said reservoir and said second pressure relief valve means is arranged to provide unidirectional fluid communication between said bladder means and said reservoir, wherein said first valve means enables fluid to bypass said bladder means by passing from said pump means to said reservoir whenever said fluid pressure adjacent said pump means is greater than a first predetermined amount and precluding fluid from passing therealong whenever said pressure is less than said first predetermined amount so as to establish a maximum amount of fluid pressure which can be pumped into said bladder means with said pump means and said second pressure relief valve means enabling fluid to pass therethrough in passing from said bladder means to said reservoir whenever the fluid pressure inside said bladder means is greater than a second predetermined amount and precluding fluid from passing therethrough whenever said pressure inside said bladder means is not greater than said second predetermined amount, said second predetermined amount being greater than said first predetermined amount such that when said pump means is utilized to inflate said bladder means to said first predetermined amount of pressure, fluid passes through said second valve means only when said bladder means incurs additional pressure with said additional pressure being generally attributable to compression of said bladder means.

8. The system of claim 7 wherein said first and second valve means each comprises an inlet port, an outlet port and regulator means with said regulator means both controlling the passage of fluid from said inlet port to said outlet port and precluding the passage of fluid in the reverse direction.

9. The system of claim 8 wherein said regulator means comprises a spring and a ball which communicates with said spring, such that when said spring is in an extended position, said ball is in a first location to preclude fluid from passing through said valve means and when said spring is compressed, said ball moves away from said first location to enable fluid to pass through said valve means.

10. The system of claim 9 further comprising rotatable means for adjusting the tension of said spring.

* * * * *